(12) United States Patent
Wakai

(10) Patent No.: US 9,196,057 B2
(45) Date of Patent: Nov. 24, 2015

(54) MEDICAL IMAGE DIAGNOSIS APPARATUS, MEDICAL IMAGE DISPLAY APPARATUS, MEDICAL IMAGE PROCESSING APPARATUS, AND MEDICAL IMAGE PROCESSING PROGRAM

(75) Inventor: Misako Wakai, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 148 days.

(21) Appl. No.: 13/981,451

(22) PCT Filed: Mar. 9, 2012

(86) PCT No.: PCT/JP2012/056109
§ 371 (c)(1),
(2), (4) Date: Jul. 24, 2013

(87) PCT Pub. No.: WO2012/121368
PCT Pub. Date: Sep. 13, 2012

(65) Prior Publication Data
US 2013/0315455 A1      Nov. 28, 2013

(30) Foreign Application Priority Data

Mar. 10, 2011   (JP) ................... 2011-052982

(51) Int. Cl.
*G06K 9/00*      (2006.01)
*G06T 7/60*      (2006.01)
(Continued)

(52) U.S. Cl.
CPC ............ *G06T 7/602* (2013.01); *A61B 6/5211* (2013.01); *A61B 8/5215* (2013.01);
(Continued)

(58) Field of Classification Search
None
See application file for complete search history.

(56) References Cited

U.S. PATENT DOCUMENTS

2004/0258289 A1   12/2004   Hornegger
2005/0046644 A1   3/2005    Ohishi
(Continued)

FOREIGN PATENT DOCUMENTS

CN   1538796 A   10/2004
CN   1591477 A   3/2005
(Continued)

OTHER PUBLICATIONS

Combined Chinese Office Action and Search Report issued Mar. 3, 2015 in Patent Application No. 201280011423.2 (with English translation of categories of cited documents).
(Continued)

*Primary Examiner* — Atiba O Fitzpatrick
(74) *Attorney, Agent, or Firm* — Oblon, McClelland, Maier & Neustadt, L.L.P.

(57) ABSTRACT

An inner wall extractor extracts the inner wall of a vital tissue based on medical image data. An outer wall extractor extracts the outer wall of the vital tissue based on the medical image data. A first raised portion calculator obtains information including the presence of a first raised portion in which the inner wall of the vital tissue is raised inward, based on the extracted inner wall of the vital tissue. A second raised portion calculator obtains information including the presence of a second raised portion in which the outer wall of the vital tissue is raised outward, based on the extracted outer wall of the vital tissue. A display controller superimposes the information of the first raised portion obtained by the first raised portion calculator and the information of the second raised portion obtained by the second raised portion calculator on an image of the vital tissue, and causes the image to be displayed on a display unit.

20 Claims, 14 Drawing Sheets

(51) Int. Cl.
*G06T 7/00* (2006.01)
*A61B 6/00* (2006.01)
*A61B 8/08* (2006.01)

(52) U.S. Cl.
CPC .............. *G06T 7/0012* (2013.01); *G06T 7/604* (2013.01); *A61B 6/504* (2013.01); *A61B 6/5217* (2013.01); *A61B 8/0891* (2013.01); *A61B 8/5223* (2013.01); *G06T 2207/30101* (2013.01); *G06T 2207/30172* (2013.01)

(56) References Cited

U.S. PATENT DOCUMENTS

| | | |
|---|---|---|
| 2006/0079746 A1 | 4/2006 | Perret et al. |
| 2008/0304616 A1* | 12/2008 | Van Uitert et al. ................ 378/4 |
| 2009/0082668 A1 | 3/2009 | Hamada et al. |
| 2009/0304149 A1 | 12/2009 | Herrmann et al. |
| 2010/0128963 A1 | 5/2010 | Waku et al. |
| 2010/0215225 A1 | 8/2010 | Kadomura et al. |
| 2011/0228994 A1 | 9/2011 | Tanaka et al. |

FOREIGN PATENT DOCUMENTS

| | | |
|---|---|---|
| CN | 101732061 A | 6/2010 |
| JP | 2006 110341 | 4/2006 |
| JP | 2008 67991 | 3/2008 |
| JP | 2009 502227 | 1/2009 |
| JP | 2009 72400 | 4/2009 |
| JP | 2010 178906 | 8/2010 |
| WO | 2006 118100 | 11/2006 |
| WO | 2010 047324 | 4/2010 |

OTHER PUBLICATIONS

International Search Report Issued May 29, 2012 in PCT/JP12/056109 Filed Mar. 9, 2012.

* cited by examiner

MEDICAL IMAGE DIAGNOSIS APPARATUS, MEDICAL IMAGE DISPLAY APPARATUS, MEDICAL IMAGE PROCESSING APPARATUS, AND MEDICAL IMAGE PROCESSING PROGRAM

TECHNICAL FIELD

Embodiments of the present invention relate to a medical image diagnosis apparatus, a medical image display apparatus, a medical image processing apparatus, and a medical image processing program that acquire three-dimensional medical image data of vital tissues by imaging the vital tissues.

BACKGROUND ART

There is application software for processing medical images for displaying the wall surface of a vital tissue based on three-dimensional medical image data (e.g., Patent Document 1). Using this application, it is possible to observe the roughness of the inner wall of the vital tissue having a tubular form, for example.

Examples of this application software include a fly-through image, an expanded image fillet view and a fish-eye view. The fly-through image allows the shape of the wall surface in a tube to be observed while moving along a core line set within the vital tissue tube. The expanded image fillet view allows the inner wall of the tubular tissue to be viewed by generating a tomographic view along a predetermined cross-section of the tubular tissue, setting the boundary of a particular tissue represented in the tomographic view, and expanding the particular tissue along the boundary. The fish-eye view allows the shape of the wall surface in the tube to be observed at a wide angle of, for example, 170 degrees, and the like.

PRIOR ART DOCUMENT

Patent Document

[Patent Document 1] Japanese Unexamined Patent Application Publication No. 2009-72400

SUMMARY OF THE INVENTION

Problems to be Solved by the Invention

However, for example, plaques formed on the inner vascular wall of the coronary artery is raised inward to narrow the vascular lumen in some cases and raised outward to increase the vascular diameter in other cases. Negative remodeling, which is raised inward, may be referred to as a first raised portion. Moreover, positive remodeling, which is raised outward, may be referred to as a second raised portion. Furthermore, modeling that is raised inward and outward respectively may be referred to as a third raised portion.

Thus, when observing inside blood vessels with the aforementioned application, there was a problem that it is possible to discover the first raised portion appearing to be convex relative to the inner vascular wall, however, the second raised portion is missed by observing only inside the blood vessels, since the portion dose not appear to be convex relative to the inner vascular wall.

The second raised portion is a soft plaque in many cases and often causes acute diseases, so early discovery and early treatment of these diseases are necessary. Moreover, the diseases often occur in the early stages when plaques start to form, so finding the plaques without fail makes it possible to achieve early discovery and early treatment of the diseases.

The embodiments are intended to solve the aforementioned problem, with the object of providing a medical image diagnosis apparatus, a medical image display apparatus, a medical image processing apparatus, and a medical image processing program that can display a raised portion in which the outer wall of the vital tissue is simultaneously raised at the same time as when displaying the inner wall of the vital tissue.

Means of Solving the Problems

In order to solve the aforementioned problem, the medical image diagnosis apparatus in the embodiments comprise an imaging unit, an inner wall extractor, an outer wall extractor, a first raised portion calculator, a second raised portion calculator, and a display controller, wherein the imaging unit acquires three-dimensional medical image data of vital tissues having an inner wall and an outer wall by imaging the vital tissues. The inner wall extractor extracts the inner wall of the vital tissues based on the medical image data. The outer wall extractor extracts the outer wall of the vital tissues based on the medical image data. The first raised portion calculator obtains information including the presence of a first raised portion in which the inner wall of the vital tissue is raised inward, based on the extracted inner wall of the vital tissue. The second raised portion calculator obtains information including the presence of a second raised portion in which the outer wall of the vital tissue is raised outward, based on the extracted outer wall of the vital tissue. The display controller superimposes the information of the first raised portion obtained by the first raised portion calculator and the information of the second raised portion obtained by the second raised portion calculator on the image of the vital tissue, and causes the image to be displayed on a display unit.

MODE FOR CARRYING OUT THE INVENTION

[The First Embodiment]

The embodiment of this medical image diagnosis apparatus is described with reference to each figure.

[Configuration]

Figure 1:
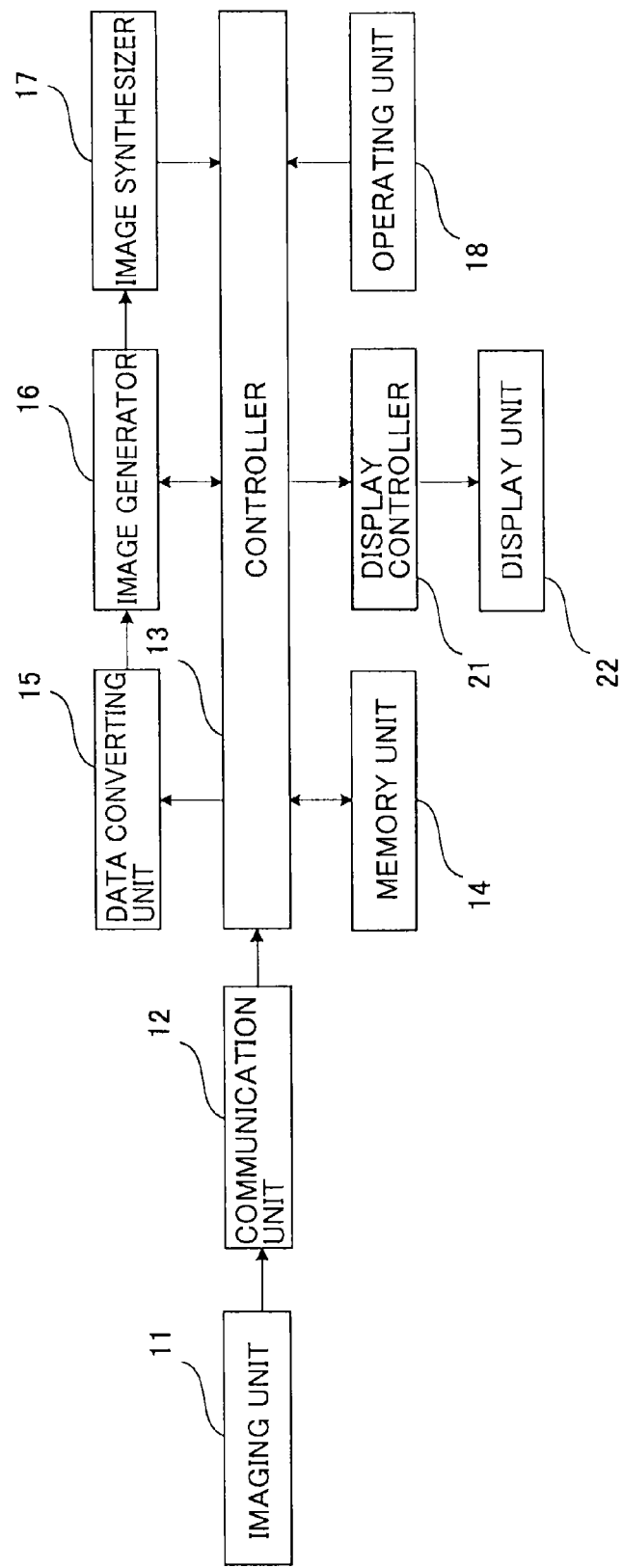
FIG. 1 is a block diagram showing a configuration of a medical image diagnosis apparatus.

FIG. 1 is a block diagram showing a configuration of the medical image diagnosis apparatus. As shown in FIG. 1, an imaging unit 11 is connected to the medical image display apparatus via a communication unit 12.

The imaging unit 11 is referred to as a modality, which is an apparatus for performing an examination on a subject and generating three-dimensional medical image data (digital data). As a modality, any apparatus conventionally used may be applied, for example, an X-ray CT (Computer Tomography) apparatus, an MRI (Magnetic Resonance Imaging) apparatus, an ultrasound diagnosis apparatus, and the like.

The X-ray CT apparatus reconfigures an internal image (tomographic view or three-dimensional image) of the subject by scanning the subject with radiation, detecting the radiation passing through the subject, and performing computer processing. The MRI apparatus reconfigures an internal image of the subject using the nuclear magnetic resonance phenomenon. The ultrasound diagnosis apparatus irradiates the subject with ultrasound waves, and then analyzes its echo state to image the inside of the body. In addition, these apparatuses are widely used conventionally, so detailed descriptions thereof are omitted.

The communication unit 12 performs data communication via LAN (Local area network). The communication unit 12 is configured to include a communication device such as a LAN card.

[Medical Image Display Apparatus]

The medical image display apparatus comprises a controller 13, a memory unit 14, a data converting unit 15, an image generator 16, an image synthesizer 17, an operating unit 18, a display controller 21, and a display unit 22. In addition, as an example, the image processing apparatus is comprised of the controller 13, the memory unit 14, the data converting unit 15, the image generator 16, the image synthesizer 17, and the operating unit 18 described above.

The memory unit 14 stores various types of information. Specifically, the memory unit 14 stores medical image data and accessory information that the communication unit 12 has received from a server (not shown). The controller 13 executes processing to store the information in the memory unit 14 along with processing to retrieve the information stored in the memory unit 14. The memory unit 14 is configured to include writable storage such as a hard disc drive.

The data converting unit 15 converts the medical image data into black-and-white image data. The black-and-white image data is often gray-scale image data expressed with a brightness value in a predetermined gray range (e.g., 0-255).

The operating unit 18 is used by an operator to operate the display unit 22 and enter various types of information. The operating unit 18 is configured to include any operating device or input device including a mouse, a keyboard, a joystick, a trackball, a dedicated control panel, or the like.

Figure 2:
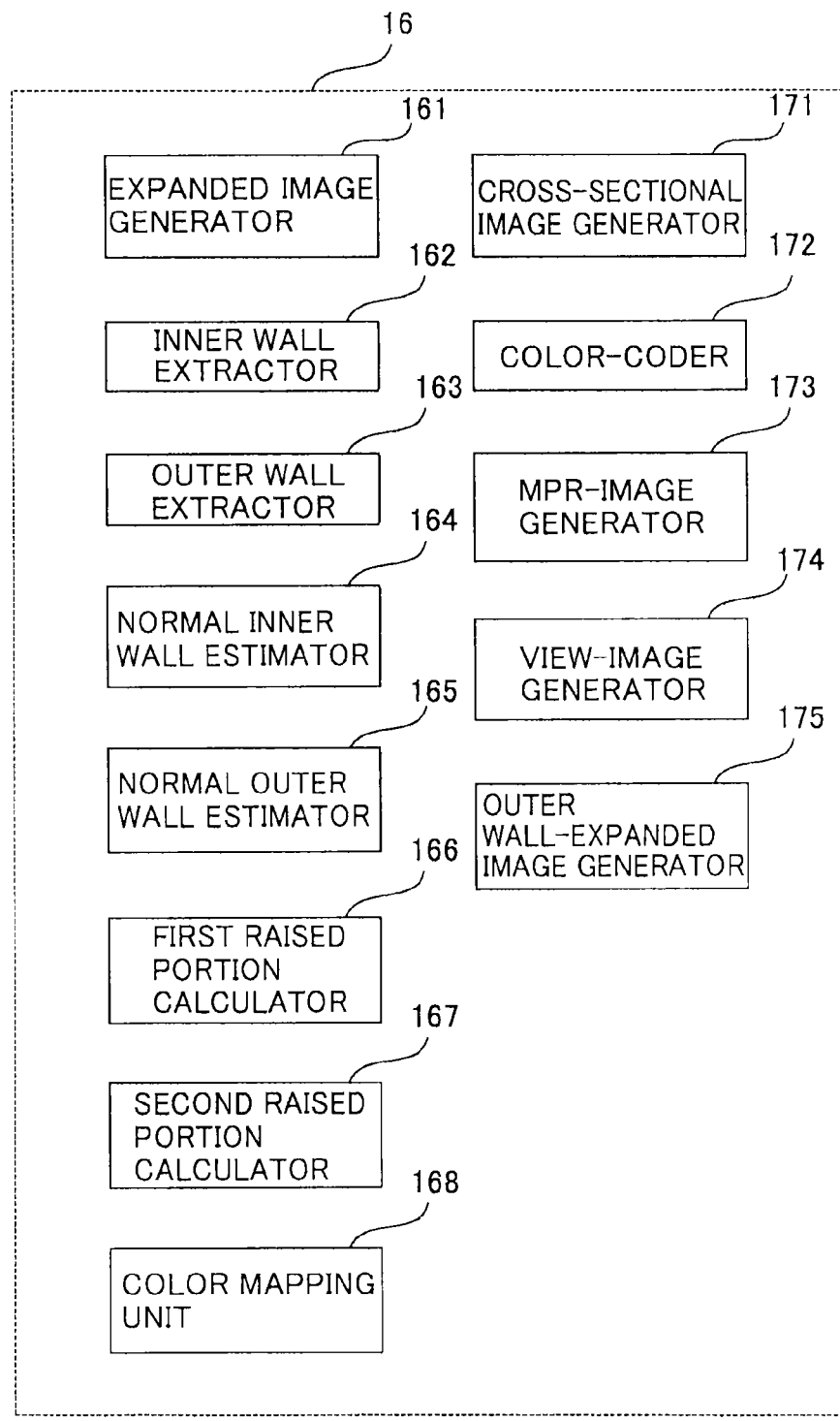
FIG. 2 is a block diagram showing a configuration of an image generator.

FIG. 2 is a block diagram showing the configuration of the image generator 16. As shown in FIG. 2, the image generator 16 comprises an expanded image generator 161, an inner wall extractor 162, an outer wall extractor 163, a normal inner wall estimator 164, a normal outer wall estimator 165, a first raised portion calculator 166, a second raised portion calculator 167, and a color mapping unit 168.

The image generator 16 is for generating a desired image based on image data of the subject imaged by the aforementioned modality. Here, an image generator 16 is described that generates an expanded image of the vital tissue and an image of a lesion on the expanded image, based on three-dimensional medical image data imaged by the X-ray CT apparatus. Further, a tubular portion in which the tissue is formed to be tubular such as the coronary artery, and the like, is described as a part of the vital tissue. In X-ray imaging performed by administering a contrast agent to the subject, obtained CT values (projection data) of the contrast agent flowing in the tubular portion, the tubular portion (including the lesion), and the thoracic cavity are different from each other. The image generator 16 generates image data of the vital tissue based on the CT values. This makes it possible to extract the vital tissue from the generated image data.

Figure 3:
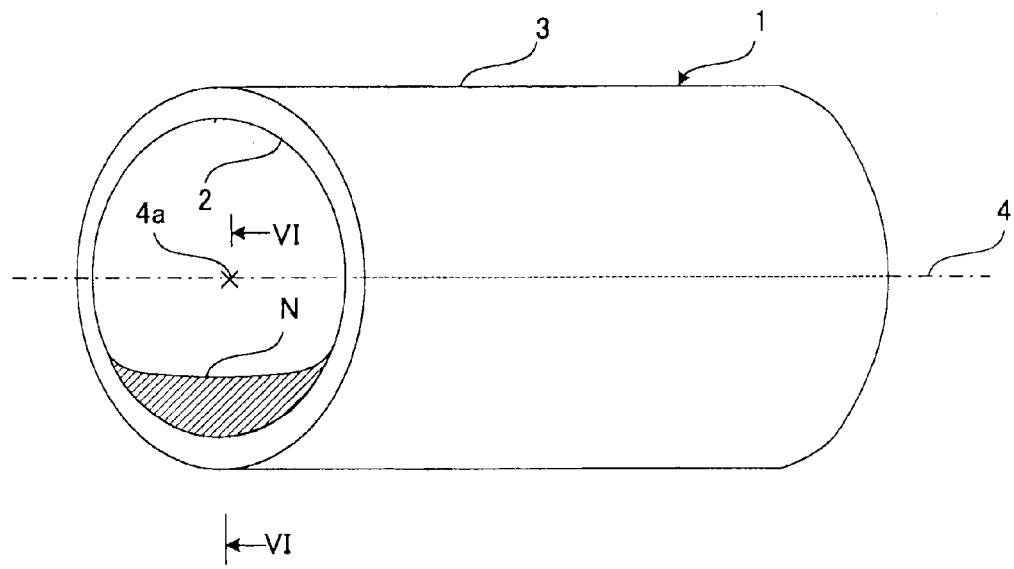
FIG. 3 is a perspective view of a tubular portion in which a first raised portion developed.
Figure 4:
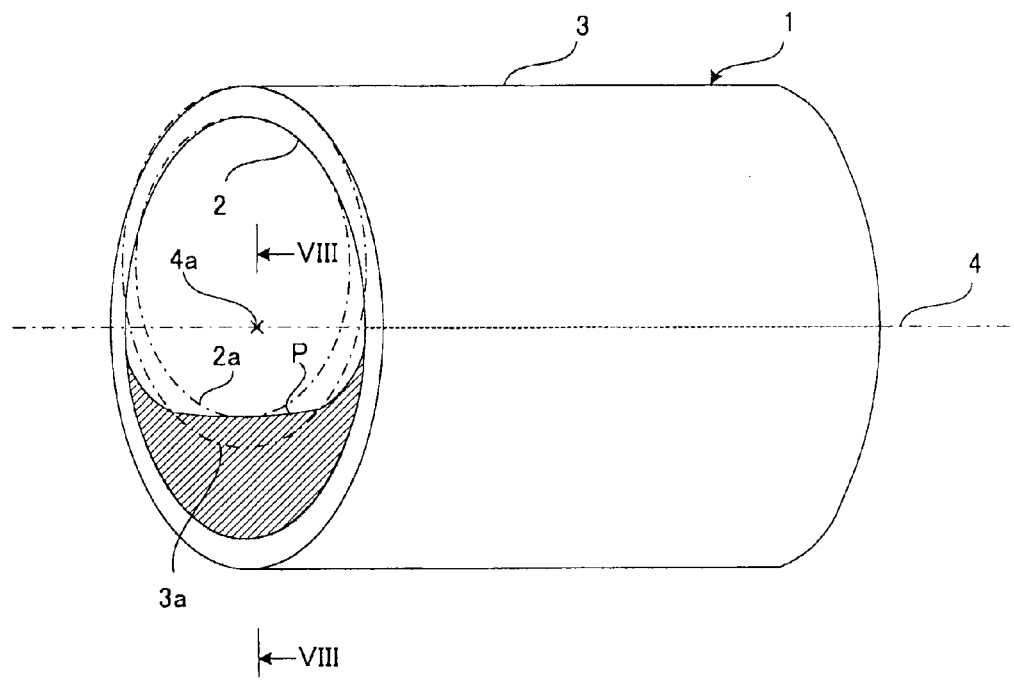
FIG. 4 is a perspective view of a tubular portion in which a second raised portion developed.
Figure 5:
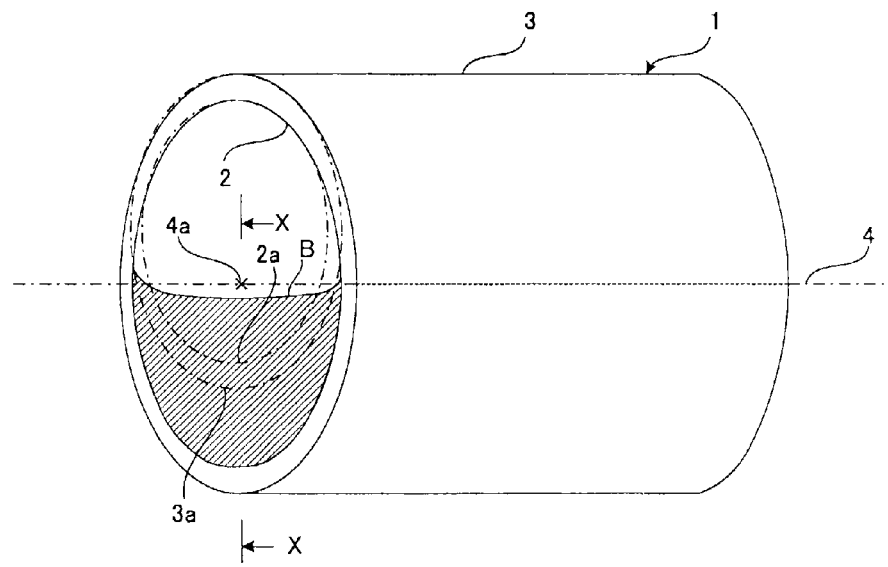
FIG. 5 is a perspective view of a tubular portion in which the first raised portion and the second raised portion developed.

FIGS. 3 to 5 are partial perspective views of a tubular portion 1 in which a lesion developed. As shown in FIGS. 3 to 5, a lesion in which plaques are accumulated is present locally in the tubular portion 1. Here, a lesion in which an inner wall 2 of the tubular portion 1 is raised inward is referred to as a first raised portion N. Moreover, a lesion in which an outer wall 3 of the tubular portion 1 is raised outward is referred to as a second raised portion P. Further, a lesion having both the first raised portion N and the second raised portion P is referred to as a third raised portion B.

The expanded image generator 161 sets the boundary for a tomographic view along a predetermined cross-section of the tubular portion 1, sets a point of view at a predetermined position for the tomographic image data along the predetermined cross-section of the tubular portion 1, and performs volume rendering on volume data along the line of sight from that point of view toward the boundary, so as to generate an expanded image in which the tubular portion 1 is expanded along a boundary. The controller 13 stores the generated expanded image in the memory unit 14.

The inner wall extractor 162 extracts the inner wall 2 of the tubular portion 1 based on medical image data (a neighbor image of the tubular portion 1, the starting point of the tubular portion 1, and a core line 4 of the tubular portion 1). Here, in the location where the lesion is developed, the inner wall of the lesion corresponds to "the inner wall of the vital tissue."

Next, extraction of the neighbor image of the tubular portion 1, detection of the starting point of the tubular portion 1, and extraction of the core line 4 of the tubular portion 1 are described. Here, the core line 4 corresponds to a line passing through a center 4a of each cross-section of the tubular portion 1 (see FIGS. 3 to 5).

For example, the controller 13, in response to the designation by the operating unit 18, extracts a neighbor image of the tubular portion 1 displayed on the display unit 22, and stores the extracted neighbor image of the tubular portion 1 in the memory unit 14 (extraction of the neighbor image of the tubular portion 1).

For example, the controller 13, in response to the operation by the operating unit 18, causes the neighbor image of the tubular portion 1 to be displayed on the display unit 22, in addition to designating a starting point of the displayed tubular portion 1, and stores the designated starting point in the memory unit 14 (detection of the starting point of the tubular portion 1). Further, a predetermined application that obtains the starting point based on the extracted tubular portion 1 may be used.

For example, the image generator 16 executes a predetermined application to extract the core line 4 of the tubular portion 1. The controller 13 stores the extracted core line 4 of the tubular portion 1 in the memory unit 14 (extraction of the core line 4 of the tubular portion 1).

As described above, an image of the tubular portion 1 to be diagnosed is extracted. In addition, processes from the close extraction of the tubular portion 1 to the extraction of the core line 4 of the tubular portion 1 are performed on each subject to be diagnosed, when there are two subjects to be diagnosed such as the left and right coronary arteries.

Based on the image of the tubular portion 1, the inner wall extractor 162 extracts the boundary of the inner wall 2 of the tubular portion 1, for example, by alternately applying a smoothing filter and a sharpening filter. In addition, because the inner wall 2 is an actual wall, constriction, or the like, is also included. The controller 13 stores the extracted inner wall 2 (including the inner wall of the first raised portion N) of the tubular portion 1 as information of the first raised portion N in the memory unit 14.

Based on the neighbor image of the tubular portion 1 and the inner wall 2 of the tubular portion 1 extracted by the inner wall extractor 162, the outer wall extractor 163 extracts the outer wall 3 of the tubular portion 1, for example, by alternately applying a smoothing filter and a sharpening filter. The controller 13 stores the extracted outer wall 3 (including the second raised portion P) of the tubular portion 1 as information of the second raised portion P in the memory unit 14.

The normal inner wall estimator 164 estimates a normal inner wall 2a, which is in the shape of the inner wall 2 before being raised as shown by the imaginary line in FIG. 4 and FIG. 5, based on the inner wall 2 of the tubular portion 1 extracted by the inner wall extractor 162. For example, for the first raised portion N, which is inwardly convex in the tubular portion 1, the normal inner wall estimator 164 estimates the normal inner wall 2a by interpolating the surroundings (regions before being raised) of the first raised portion N with a smooth plane. In addition, the normal inner wall estimator 164 may estimate an arc region spaced apart from the core line 4 by a predetermined length in the outward direction as the normal inner wall 2a. The controller 13 stores the estimated normal inner wall 2a in the memory unit 14.

The outer wall estimator 165 estimates a normal outer wall 3a, which is in the shape of the outer wall 3 before being raised as shown by the imaginary line in FIG. 4 and FIG. 5, based on the outer wall 3 of the tubular portion 1 extracted by the outer wall extractor 163. Similarly to when estimating the normal inner wall 2a, for example, for the second raised portion P, which is outwardly convex in the tubular portion 1, the normal outer wall estimator 165 estimates the normal outer wall 3a by interpolating the surroundings (regions before being raised) of the second raised portion P with a smooth plane. In addition. similarly, the normal outer wall estimator 165 may estimate an arc region spaced apart from the core line 4 by a predetermined length in the outward direction as the normal outer wall 3a. The controller 13 stores the estimated normal outer wall 3a in the memory unit 14.

The first raised portion calculator 166 obtains a first thickness T1, which is the height at which the first raised portion N is raised from the normal inner wall 2a, based on the inner wall and the normal inner wall 2a of the first raised portion N retrieved from the memory unit 14. The controller 13 stores the obtained first thickness T1 as the information of the first raised portion N in the memory unit 14. When the first thickness T1 is more than 0, the information (T1>0) will be the information indicating that the a first raised portion N is present.

The second raised portion calculator 167 obtains a second thickness T2, which is the height at which the second raised portion P is raised from the normal outer wall 3a, based on the inner wall and the normal outer wall 3a of the second raised portion P retrieved from the memory unit 14. The controller 13 stores the obtained second thickness 12 as the information of the second raised portion P in the memory unit 14. When the second thickness T2 is more than 0, the information (T2>0) will be the information indicating that the second raised portion P is present.

The color mapping unit 168 creates a first color for the first thickness T1 and a second color for the second thickness T2. The color mapping unit 168 has a table (color map) that defines the correspondence between color numbers (0-15) and actual colors, and for example, the color mapping unit 168 assigns the color number 1 to the first color (e.g., blue) and assigns the color number 2 to the second color (e.g., red). The controller 13 relates the assigned color number to pixels representing the region of the tubular portion 1, and stores the number in the memory unit 14.

The color mapping unit 168 creates the first color by dividing the thickness direction of the first thickness T1 in stages, e.g., every 2 [mm], and color-coding the region in each stage.

Figure 6:
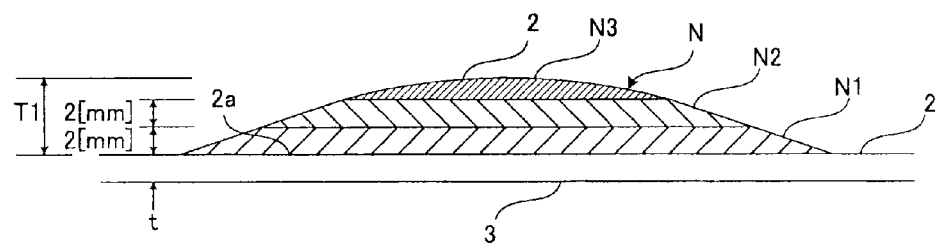
FIG. 6 is a cross-sectional view along the line VI-VI in FIG. 3 for describing a first color created by color-coding each stage.

FIG. 6 is a cross-sectional view along the line VI-VI in FIG. 3 for describing a first color created by color-coding each stage. As shown in FIG. 6, for example, the color mapping unit 168 assigns the color number of the color such that intensity of the first color (blue) becomes higher in the thickness direction (N1-N3) to the region in each stage of the first raised portion N. The controller 13 relates the assigned color number to pixels representing the region in each stage of the first raised portion N, and stores the number in the memory unit 14.

The image synthesizer 17 creates an image synthesized with the expanded image of the tubular portion 1 retrieved from the memory unit 14 and the information of the first raised portion N retrieved from the memory unit 14. The controller 13 stores the synthesized image in the memory unit 14. The display controller 21 causes the synthesized image to be displayed on the display unit 22.

Figure 7:
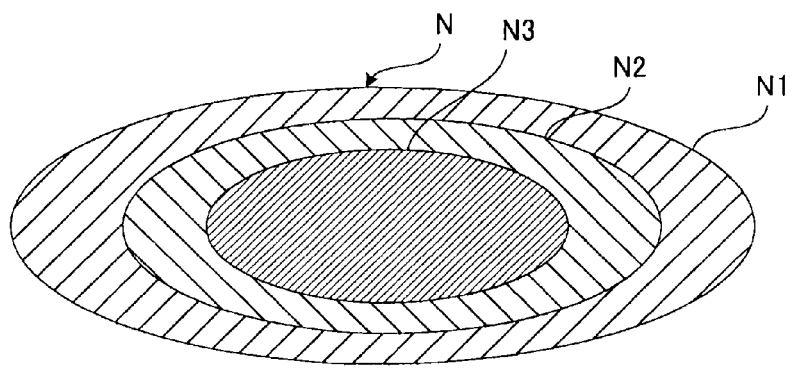
FIG. 7 is a plane view of the first raised portion displayed by being superimposed on an expanded image of the tubular portion.

FIG. 7 is a plane view of the first raised portion N displayed by being superimposed on an expanded image of the tubular portion 1. As shown in FIG. 7, the first raised portion N displayed on the display unit 22 is colored with the first color (N1-N3) with its intensity varied in stages.

The color mapping unit 168 creates the first color by dividing the thickness direction of the first thickness T1 into stages, for example, every 2 [mm], and color-coding the region in each stage. Coloring the first raised portion N with the first color varied in stages allows the height of the first raised portion N to be represented. In addition, the height of the first raised portion N may be represented in contour.

Figure 8:
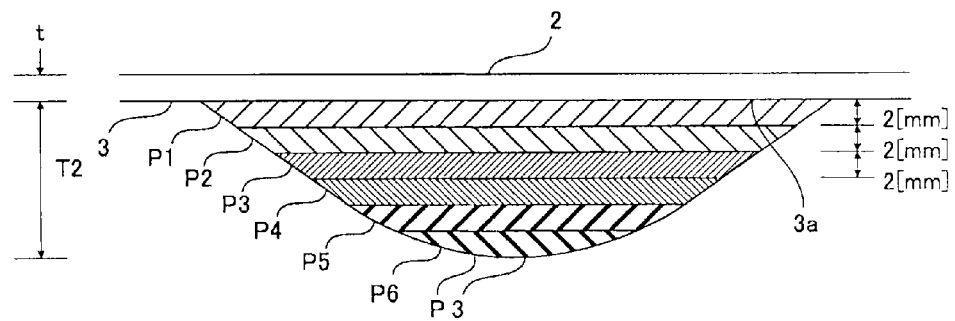
FIG. 8 is a cross-sectional view along the line VIII-VIII in FIG. 4 for describing a second color created by color-coding each stage.

FIG. 8 is a cross-sectional view along the line VIII-VIII in FIG. 4 for describing a second color created by color-coding each stage. As shown in FIG. 8, for example, the color mapping unit 168 assigns the color number of the color such that the intensity of the second color (red) becomes higher in the thickness direction (P1-P6) to the region in each stage of the second raised portion P. The controller 13 relates the assigned color number to pixels representing the region of the region in each stage of the second raised portion P, and stores the number in the memory unit 14.

The image synthesizer 17 creates an image synthesized with the expanded image of the tubular portion 1 retrieved from the memory unit 14 and the information of the second raised portion P retrieved from the memory unit 14. The controller 13 stores the synthesized image in the memory unit 14. The display controller 21 causes the synthesized image to be displayed on the display unit 22.

Figure 9:
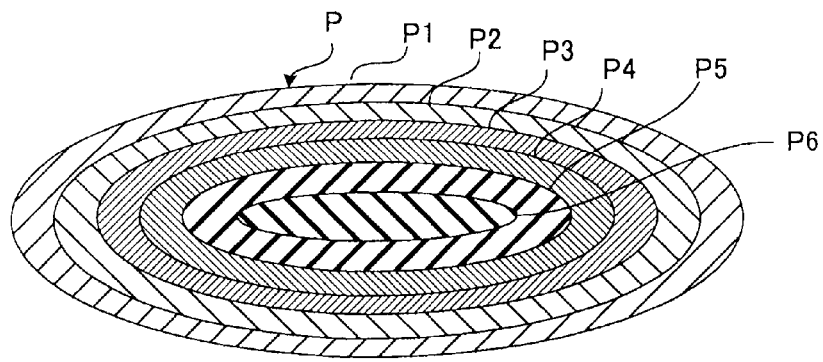
FIG. 9 is a plane view of the second raised portion displayed by being superimposed on an expanded image of the tubular portion.

FIG. 9 is a plane view of the second raised portion P displayed by being superimposed on an expanded image of the tubular portion 1. As shown in FIG. 9, the second raised portion P displayed on the display unit 22 is colored with the second color (P1-P6) with its intensity varied in stages. This allows the height of the second raised portion P to be represented. In addition, the height of the second raised portion P may be represented in contour.

Any one of the first raised portion N and the second raised portion P, which is displayed by being superimposed on the expanded image of the tubular portion 1, has been described above.

However, since it is common for the first raised portion N to develop after the second raised portion P has developed in the tubular portion 1, it is less common, practically, for only the first raised portion N to be displayed. That is, when the first raised portion N is displayed, the second raised portion P is often displayed together. When both the first raised portion N and the second raised portion P are displayed simultaneously, both may be mixed with each other and distinguished with difficulty.

Figure 10:
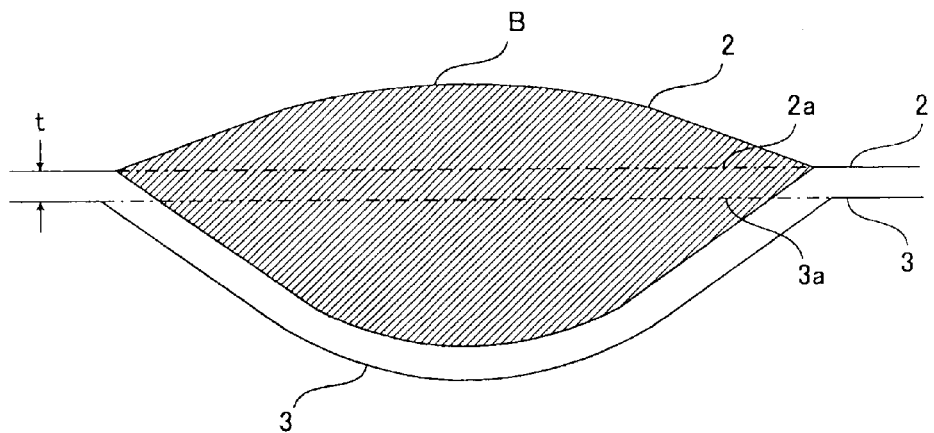
FIG. 10 is a cross-sectional view along the line X-X in FIG. 5 for describing a third color that is created.

FIG. 10 is a cross-sectional view along the line X-X in FIG. 5 for describing a third color that is created. As shown in FIG. 10, a third raised portion B (the first raised portion N and the second raised portion P) developed in the tubular portion 1. In addition, the color mapping unit 168 determines that the third raised portion B developed when the first thickness T1 is more than 0 (T1>0) as well as when the second thickness T2 is more than 0 (T2>0).

The color mapping unit 168 creates a third color for the region where the third raised portion B developed. The color mapping unit 168 assigns the color number 3 to the third color (e.g., purple). The controller 13 relates the assigned color number to pixels representing the region of the tubular portion 1, and stores the number in the memory unit 14.

The image synthesizer 17 creates an image synthesized with the expanded image of the tubular portion 1 retrieved from the memory unit 14 and the information of the third raised portion B retrieved from the memory unit 14. The controller 13 stores the synthesized image in the memory unit 14. The display controller 21 causes the synthesized image to be displayed on the display unit 22.

Figure 11:
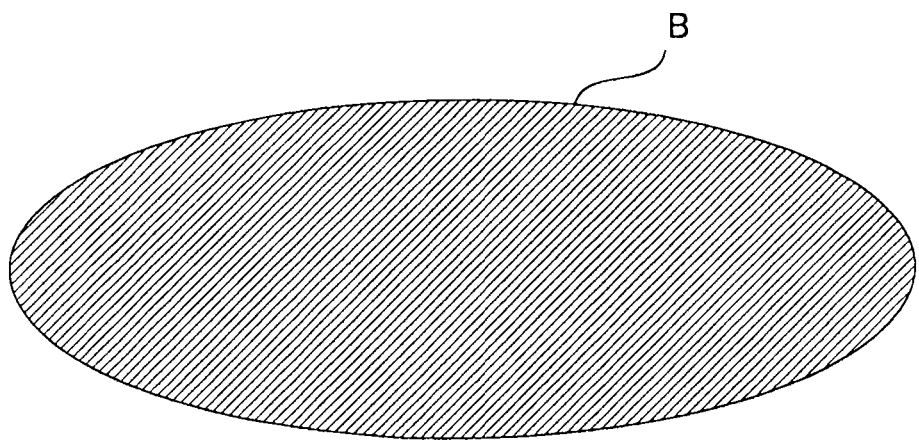
FIG. 11 is a plane view of a range indicating the first raised portion and the second raised portion displayed by being superimposed on an expanded image of the tubular portion.

FIG. 11 is a plane view of the third raised portion B displayed by being superimposed on an expanded image of the tubular portion 1. As shown in FIG. 11, the range of the third raised portion B displayed on the display unit 22 is colored with the third color (purple). In addition, the color mapping unit 168 may color the third raised portion B by enhancing the intensity of the third color depending on a thickness T3 of the third raised portion B.

The thickness T3 can be obtained from the following expression.

$$T3 = T1 + T2 \tag{1}$$

In addition, a thickness (predetermined thickness) t of the wall portion of the tubular portion 1 may be added to the right side of the above-mentioned expression (1).

[Operation]

Figure 12:
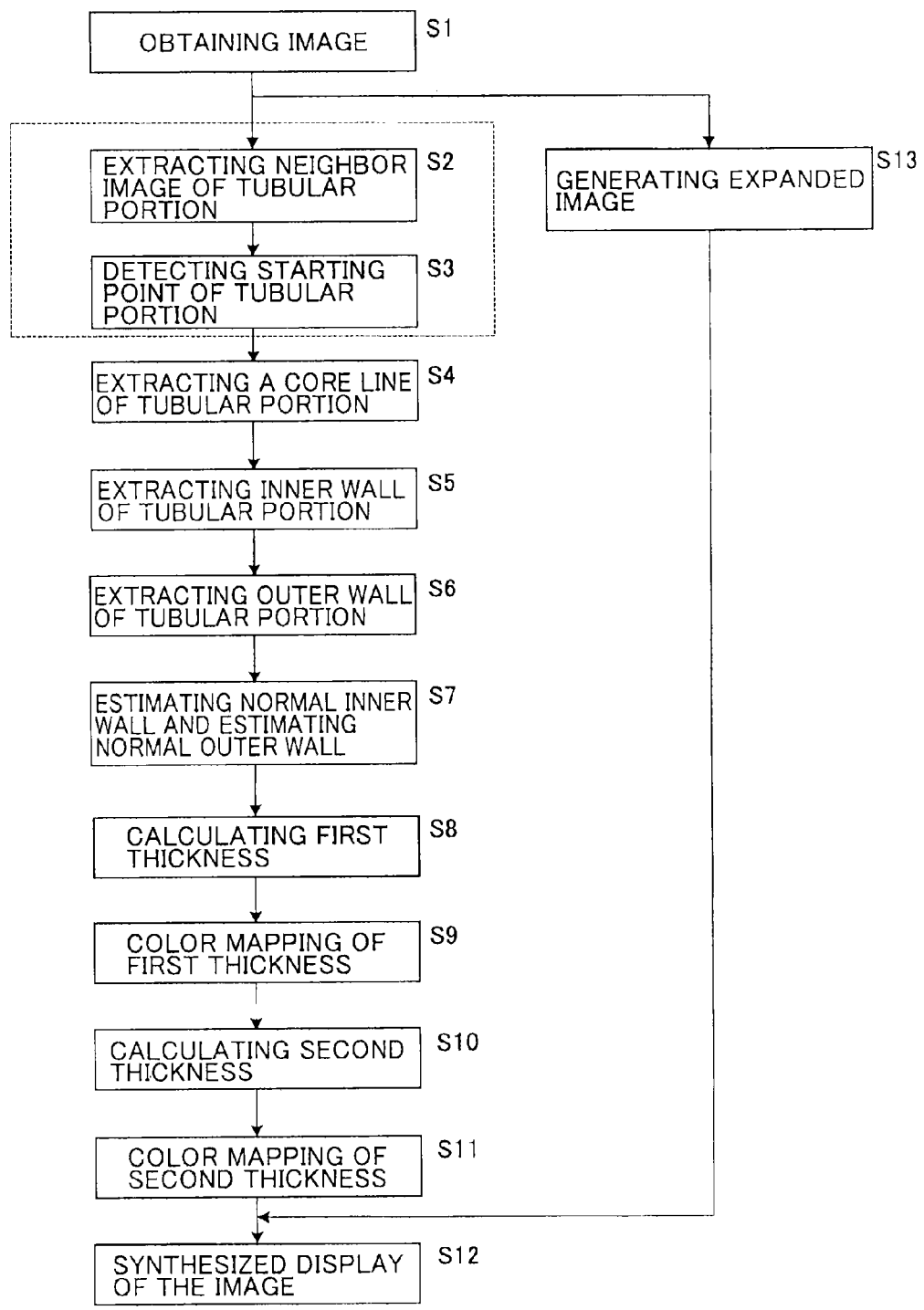
FIG. 12 is a flowchart indicating an operation of a medical image display apparatus.

Next, the operation of the medical image diagnosis apparatus to generate an expanded image of the tubular portion 1 and an image of a lesion on the expanded image, based on three-dimensional medical image data imaged by the X-ray CT apparatus, and cause the each generated image to be displayed, is described with reference to FIG. 12. FIG. 12 is a flowchart indicating the operation of the image processing apparatus.

(Obtaining a CT image: Step S1)

As shown in FIG. 12, the three-dimensional medical image data of the subject imaged by the X-ray CT apparatus and stored in a server (not shown) is stored in the memory unit 14 via the communication unit 12.

(Extracting a Neighbor Image of the Tubular Portion: Step S2)

In response to the designation by the operating unit 18, the controller 13 extracts a neighbor image of the tubular portion 1 displayed on the display unit 22.

(Detecting a Starting Point of the Tubular Portion: Step S3)

Next, in response to the operation by the operating unit 18, the starting point of the extracted neighbor image of the tubular portion 1 is designated.

(Extracting a Core Line of the Tubular Portion: Step S4)

Next, the image generator 16 extracts the core line 4 of the tubular portion 1. The coordinates (xg, yg) of the center 4a of the tubular portion 1 can be obtained from the following expressions, for example.

$$xg = Sy/A \tag{2}$$

$$yg = Sx/A \tag{3}$$

Here, Sx denotes the geometrical moment of area relative to the x-axis, Sy the geometrical moment of area relative to the y-axis, and A the total cross-sectional area of the tubular portion 1 (including the lesion and lumen).

(Extracting the Inner Wall of the Tubular Portion: Step S5)

Next, the inner wall extractor 162 extracts the inner wall 2 of the tubular portion 1 based on the image of the tubular portion 1. The inner wall 2 in this case is not the inner wall of the coronary artery but an actual wall, so the inner wall of the first raised portion N that is raised inward in the tubular portion 1 is also included.

(Extracting the Outer Wall of the Tubular Portion: Step S6)

Next, the outer wall extractor 163 extracts the outer wall 3 of the tubular portion 1 based on the image of the tubular portion 1. The outer wall 3 in this case also includes the outer wall 3 that is raised outward in the tubular portion 1 by the second raised portion P.

(Estimating the Normal Inner Wall and Estimating the Normal Outer Wall: Step S7)

Next, the normal inner wall estimator 164 estimates the normal inner wall 2a that is in the shape of the inner wall 2 before being raised, based on the inner wall 2 of the tubular portion 1, which is an actual wall. Moreover, the normal outer wall estimator 165 estimates the normal outer wall 3a that is in the shape of the outer wall 3 before being raised, based on the outer wall 3 of the tubular portion 1.

(Calculating the First Thickness: Step S8)

The first raised portion calculator 166 obtains the first thickness T1, which is the height of the first raised portion N, based on the inner wall 2 and the normal inner wall 2a of the first raised portion N.

(Color Mapping of the First Thickness: Step S9)

The color mapping unit 168 creates the first color (e.g., blue) for the first thickness T1. For example, the color mapping unit 168 assigns the color number of the first color to each pixel representing the region of the first raised portion N, and the controller 13 relates the color number to each pixel, and stores the number in the memory unit 14.

(Calculating the Second Thickness: Step S10)

The second raised portion calculator 167 obtains the second thickness T2, which is the height of the second raised portion P, based on the outer wall 3 and the normal outer wall 3a of the second raised portion P.

(Color Mapping of the Second Thickness: Step S11)

The color mapping unit 168 creates the second color (e.g., red) for the second thickness T2. For example, the color mapping unit 168 assigns the color number of the second color to each pixel representing the region of the second raised portion P, and the controller 13 relates the color number to each pixel and stores the number in the memory unit 14.

(Generating an Expanded Image: Step S13)

In parallel with Steps S1-S11 described above, the expanded image generator 161 generates an expanded image in which the tubular portion 1 is expanded based on the image data of the tubular portion 1.

(Synthesized Display of the Image: Step S12)

The image synthesizer 17 superimposes the information of the first raised portion N and the information of the second raised portion P on the expanded image of the tubular portion 1, and displays the image.

Here, the information of the first raised portion N includes the image of the first raised portion N, the information that the first raised portion N is present in the tubular portion 1 (information of the presence), as well as the first thickness T1, and the information indicating the degree of the thickness T1. Similarly, the information of the second raised portion P includes the image of the second raised portion P, the information that the second raised portion P is present in the tubular portion 1 (information of the presence), as well as the second thickness T2, and the information indicating the degree of the thickness T2.

In addition, as an example, the image processing program is configured to cause a computer to execute the processing from Step S1 to Step S12 described above.

[The Second Embodiment]

When causing the first raised portion N and the second raised portion P to be displayed simultaneously on the image of the tubular portion 1, the range of the third raised portion B was colored with the third color (purple) in order to represent the fact that both the first raised portion N and the second raised portion P have developed, and also, the range of the third raised portion B was colored by enhancing the intensity of the third color depending on the thickness T3 of the third raised portion B; however, it is difficult to distinguish the first raised portion N from the second raised portion P, making it difficult to determine the state of progress of each lesion in the first raised portion N and the second raised portion P.

Next, a medical image diagnosis apparatus according to the second embodiment is described. In the following description, the same numbers are provided to the elements having the same configuration as those of the first embodiment, and the descriptions thereof are omitted.

Figure 13:
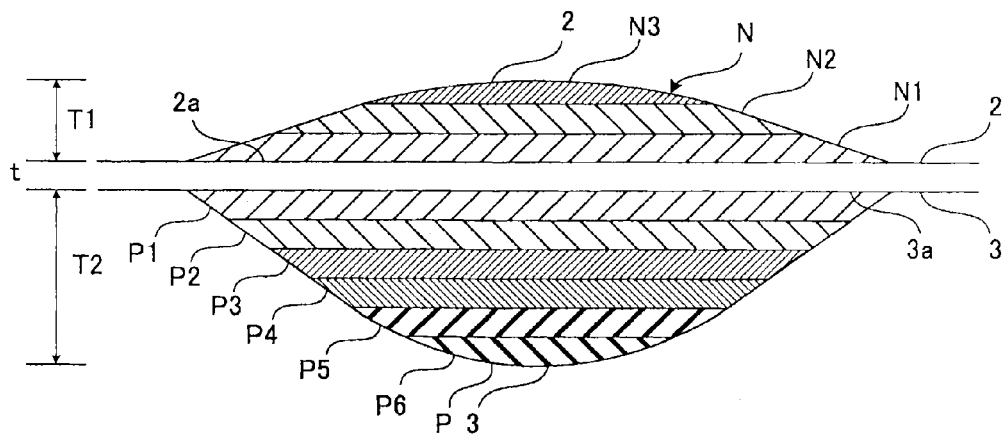
FIG. 13 is a diagram showing an example of display modes when displaying the first raised portion and the second raised portion simultaneously in the medical image diagnosis apparatus according to the second embodiment.

FIG. 13 is a diagram showing an example of display modes when displaying the first raised portion N and the second raised portion P simultaneously. As shown in FIG. 13, the first raised portion N indicated by the first color (e.g., blue) and the second raised portion P indicated by the second color (e.g., red) are displayed by being superimposed on a tomographic view (an image of the tubular portion 1) in which the wall of the tubular portion 1 is cut into sections along the core line 4.

It is decided which part of a tomographic view in the tubular portion 1 is created by that, in response to the operation by the operating unit 18 on the display unit 22, the controller 13 designates a position in the tubular portion 1, and in response to the designated position, the image generator 16 creates a tomographic view in which the tubular portion 1 is cut into sections at the position.

The image generator 16 creates a tomographic view as an image of the tubular portion 1, creates the first raised portion N and the second raised portion P relative to the tomographic view, and synthesizes the tomographic view with the first raised portion N and the second raised portion P. The display controller 21 causes the synthesized image to be displayed on the display unit 22. In addition, the first color and the second color may be different in tone in stages.

As described above, displaying the first raised portion N and the second raised portion P by being superimposed on the tomographic view makes it possible to easily view the state of progress of each lesion in the first raised portion N and the second raised portion P.

Further, in response to the operation by the operating unit 18, the controller 13 changes a cross-section when creating a tomographic view, and in response to the changed cross-section, the image generator 16 creates a tomographic view of the tubular portion 1, the first raised portion N, and the second raised portion P, while the display controller 21 causes the first raised portion N and the second raised portion P to be superimposed on the tomographic view and displayed on the display unit 22. Thereby, the state of progress of each lesion will be observed from different angles, allowing the state of progress of the lesion to be viewed more accurately.

Figure 14:
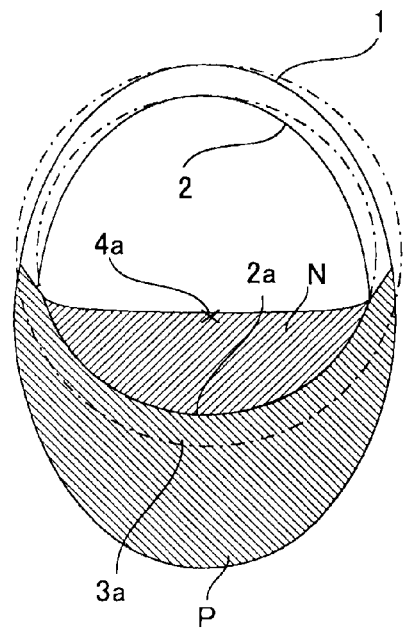
FIG. 14 is a diagram showing another example of the display modes when simultaneously displaying the first raised portion and the second raised portion.

FIG. 14 is a diagram showing another example of the display modes when displaying the first raised portion N and the second raised portion P simultaneously. As shown in FIG. 14, the first raised portion N indicated by the first color (e.g., blue) and the second raised portion P indicated by the second color (e.g., red) are displayed by being superimposed on a tomographic view (an image of the tubular portion 1) in which the wall of the tubular portion 1 is cut into sections in the direction perpendicular to the core line 4. In addition, the first color and the second color may be different in tone in stages.

In addition, although in the aforementioned embodiment, the first raised portion N and the second raised portion P were simultaneously displayed in the image of the tubular portion 1, in the display mode displaying those two portions together on a plane, it is difficult to distinguish the first raised portion N from the second raised portion P, making it difficult to determine the state of progress of each lesion in the first raised portion N and the second raised portion P.

Consequently, the image synthesizer 17 creates both a synthesized image in which an image of the first raised portion N is superimposed on an image of the tubular portion 1 and a synthesized image in which an image of the second raised portion P is superimposed on an image of the tubular portion 1, while the display controller 21 alternatively displays those synthesized images in a switching manner on the display unit 22. This makes it possible to easily determine the state of progress of each lesion in the first raised portion N and the second raised portion P.

Moreover, in the embodiment, the image generator 16, based on the information when the first raised portion N is present (T1>0) and the information when the second raised portion P is present (T2>0), creates a first identifying label for identifying the presence of the first raised portion N and a second identifying label for identifying the presence of the second raised portion P, while the display controller 21 causes the first identifying label and the second identifying label to be superimposed on the image of the tubular portion 1, and displayed the labels on the display unit 22. This makes it possible to distinguish the first raised portion N from the second raised portion P.

Furthermore, the display controller 21 may cause the information representing the first thickness T1 (e.g., a numerical value) and the information representing the degree of the first thickness T1 (e.g., N1, N2, N3 . . . ), as well as the information representing the second thickness T2 (e.g., a numerical value) and the information representing the degree of the second thickness T2 (e.g., P1, P2, P3 . . . ) to be displayed by being superimposed on the image of the tubular portion 1. The first thickness T1 of the first raised portion N and the second thickness T2 of the second raised portion P are displayed in contrast to each other, for example, as 2 [mm]/3 [mm], or the degree of the first thickness T1 and the degree of the second thickness T2 are displayed in contrast to each other, for example, as N3/P5, making it easy to determine the state of progress of the lesion.

[The Third Embodiment]

In the first and second embodiments described above, it was indicated that, when causing the inner wall of the vital tissue to be displayed, a raised portion with the outer wall raised is simultaneously displayed on the image of the vital tissue. In contrast to this, in the following embodiment, it is indicated that an image of the vital tissue is displayed in which the regions of its components of the vital tissue are color-coded. Thereby, lesions can be found without fail by easily viewing the vital tissue that has become a calcified component or a lipid component. Consequently, it is possible to achieve early discovery and early treatment of diseases.

An example image of the vital tissue can be any one of a cross-sectional image, an expanded image, an MPR image, a view image, an expanded image of the outer wall. or combination of these images. In addition, the cross-sectional image, the expanded image, the MPR image, the view image, and the expanded image of the outer wall are described in detail later.

Figure 15:
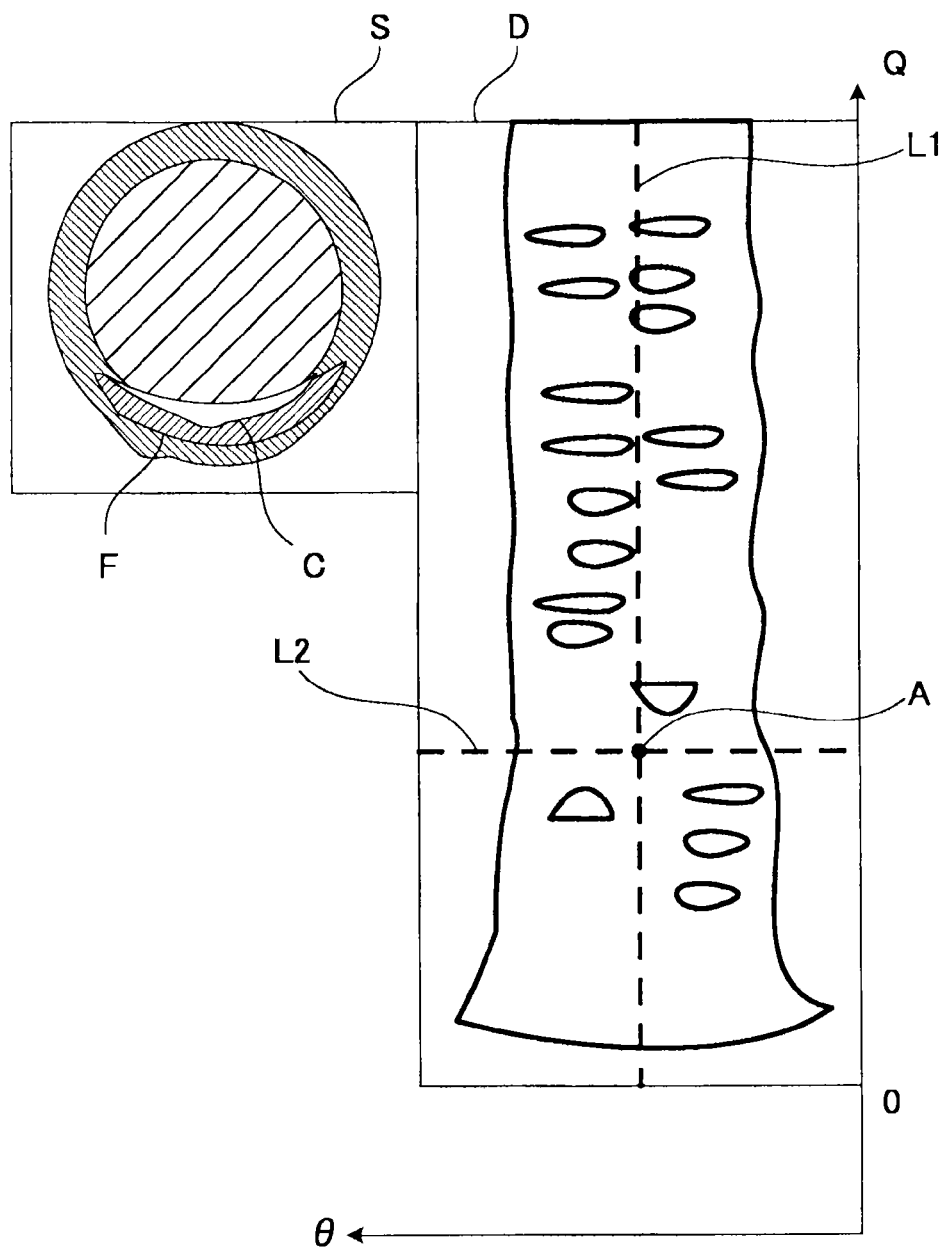
FIG. 15 is a diagram showing an example of the display modes when a cross-sectional image is displayed along with an expanded image in the medical image diagnosis apparatus according to the third embodiment.

Next, a medical image diagnosis apparatus according to the third embodiment is described with reference to FIG. 15. FIG. 15 is a diagram showing an example of the display modes when a cross-sectional image is displayed along with an expanded image. In addition, the configuration of the third embodiment different from the embodiments described above is mainly described, with descriptions of the configuration similar to the embodiments described above omitted.

In the third embodiment, the image generator 16 comprises a cross-sectional image creating unit 171 and a color-coder 172.

The cross-sectional image creating unit 171 creates an image when the vital tissue is cut into sections at a designated position (including a predetermined position) based on three-dimensional medical image data. In addition, the three-dimensional medical image data may be referred to as three-dimensional data or volume data. The position of the cross-section is defined by three-dimensional coordinates designated based on the three-dimensional medical image data.

The expanded image generator 161 generates an expanded image in which the inner wall 2 of the tubular portion 1 is expanded in a planar manner based on the three-dimensional medical image data (described above). An example of the expanded image is an image in which, based on the three-dimensional medical image data, values of projection processing performed in the radial direction from the central axis of the tubular portion 1 are distributed, with the circumferential angle around the central axis as the horizontal axis and a position on the central axis as the vertical axis. In addition, the position on the central axis is defined by three-dimensional coordinates designated based on the three-dimensional medical image data.

The color-coder 172 classifies (distinguishes) components of the vital tissue (e.g., calcium and fat) based on brightness values and color-codes the regions of these components by classification in a cross-sectional image created by the cross-sectional image creating unit 171. For example, the region of the calcium component and the region of the fat component of the vital tissue are displayed in different colors, "white" and "yellow," in a distinguishable manner.

The display controller 21 causes the expanded image to be displayed along with a cross-sectional image in which the regions of the components of the vital tissue are color-coded (see FIG. 15).

Further, in response to operating the unit (input section) 18, the display controller 21 causes the position of the cross-section to be displayed on the expanded image so that the position can be designated. The position designated on the expanded image (the position on the central axis) and the position of the cross-section are related by three-dimensional coordinates. Therefore, the cross-sectional image generator 171, in response to the position designated on the expanded image, creates a cross-sectional image when biological information is cut into sections at the position of the cross-section related to that position.

The display controller 21 causes the expanded image, the position designated on the expanded image, and the cross-sectional image to be displayed when the biological information is cut into sections at the position of the cross-section corresponding to the designated position (see FIG. 15).

FIG. 15 indicates the cross-sectional image as "S," the expanded image as "D," the region of the calcium component as "C," and the region of the fat component as "F." Further in FIG. 15, the designated position represented on the expanded image is indicated as "A," the central axis of the tubular portion 1 as "L0," the line along the central axis L0 as "L1," and the line through the position A and perpendicular to the line L1 as "L2." In addition, the central axis L0 may be referred to as the core line 4.

[Variation]

Figure 16:
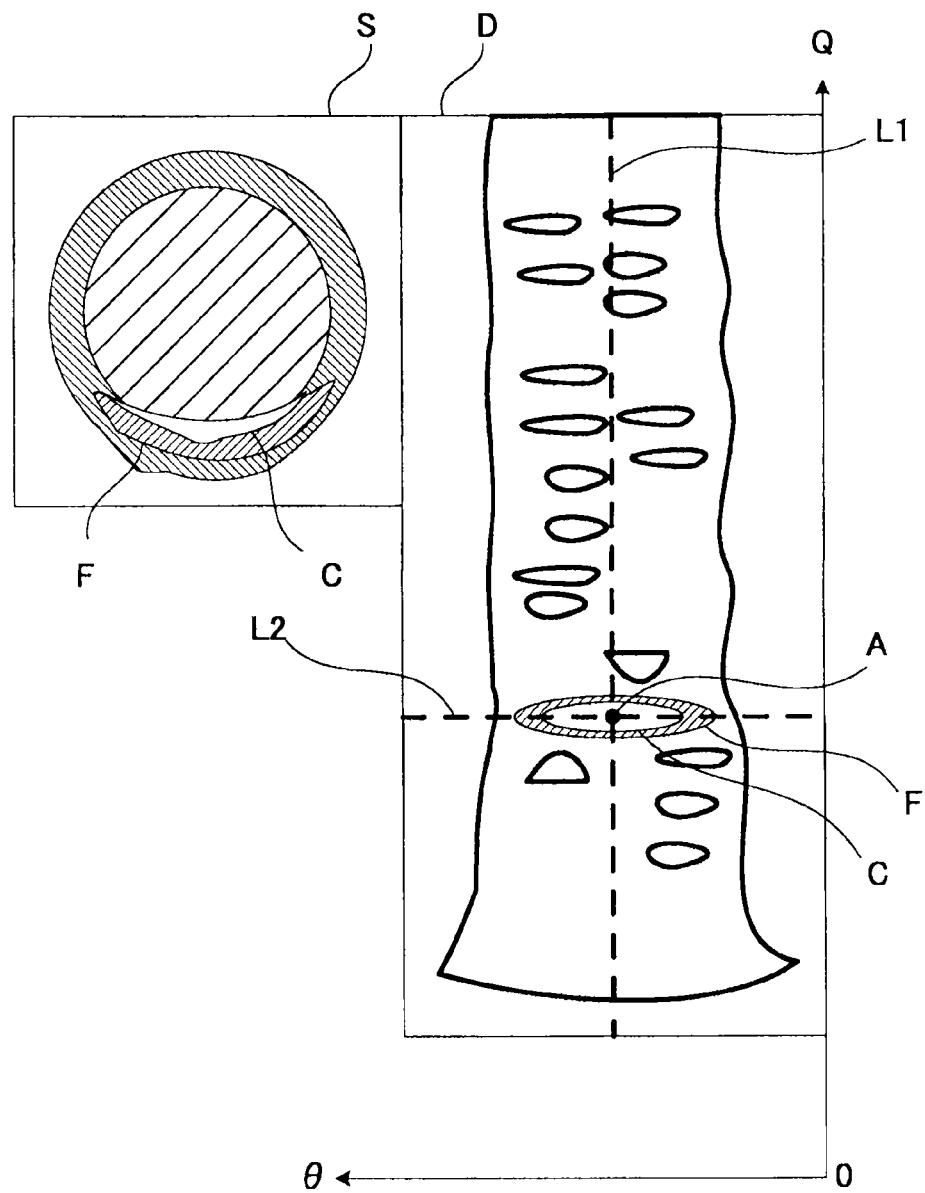
FIG. 16 is a diagram showing an example of the display modes when the regions of the components of a vital tissue on the expanded image shown in FIG. 15 are color-coded.

Next, a variation of the third embodiment is described with reference to FIG. 16. FIG. 16 is a diagram showing an example of the display modes when the regions of the components of the vital tissue on the expanded image shown in FIG. 15 are color-coded.

Although in the embodiment described above, the color-coder 172 color-codes the regions of the components of the vital tissue on the cross-sectional image by classification, and in this variation, the color-coder 172 further color-codes the regions of the components of the vital tissue on the expanded image by classification.

For color-coding on the expanded image, similar to color-coding on the cross-sectional image described above, it is preferable that regions of the same component be of the same color (e.g., "white" for regions of calcium components and "yellow" for regions of fat components). Thereby, comparing the cross-sectional image with the expanded image allows the components (e.g., calcified component and/or lipid component) of the vital tissue to be easily viewed. In FIG. 16, the expanded image "D" that is color-coded in a similar manner to the cross-sectional image "S" is shown.

[The Fourth Embodiment]

In the third embodiment described above, the expanded image was indicated as an image of the vital tissue to be displayed along with the cross-sectional image. In contrast to this, in the fourth embodiment, it is indicated that an MPR (Multi Planar Reconstruction) is further displayed. In addition, the MPR image may be displayed instead of the expanded image.

Figure 17:
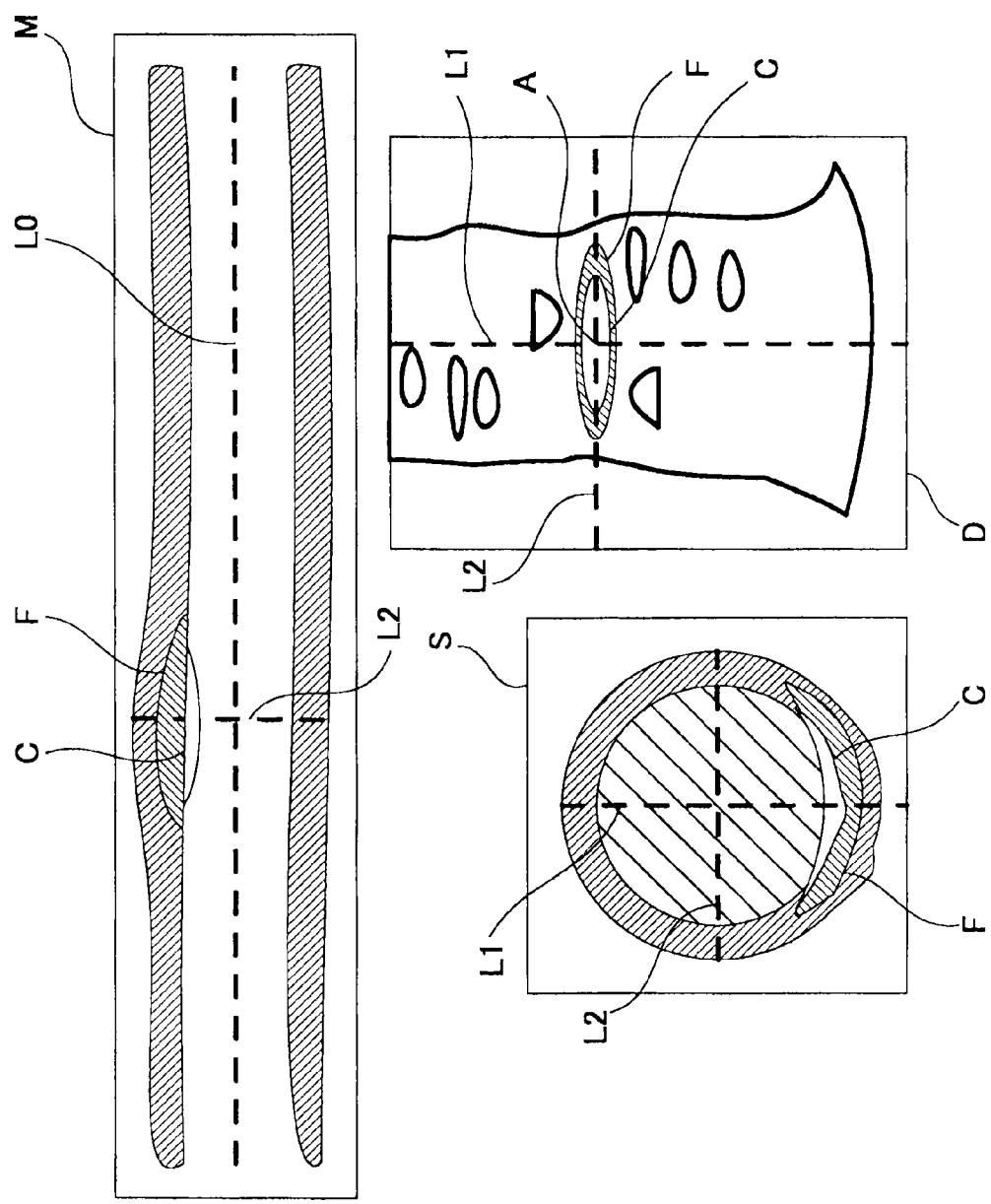
FIG. 17 is a diagram showing an example of the display modes when a cross-sectional image is displayed along with an expanded image and an MPR image in the medical image diagnosis apparatus according to the fourth embodiment.

Next, the medical image diagnosis apparatus according to the fourth embodiment is described with reference to FIG. 17. FIG. 17 is a diagram showing an example of the display modes when a cross-sectional image is displayed along with an expanded image and an MPR image in the medical image diagnosis apparatus according to the fourth embodiment. In addition, the configuration of the fourth embodiment different from the embodiments described above is mainly described, with the descriptions of the configuration similar to the embodiments described above omitted.

In this embodiment, the image generator 16 comprises an MPR-image generator 173. The MPR-image generator 173, in response to the designation of the position of the cross-section by the operation of the operating unit (input section) 18, creates an MPR image representing a plurality of cross-sections of the vital tissue based on the three-dimensional medical image data.

The color-coder 172 classifies (distinguishes) components of the vital tissue on the MPR image based on brightness values, and color-codes the regions of those components by classification.

Color-coding on the MPR image is preferably similar to color-coding on the cross-sectional image and/or expanded image described above (e.g., "white" for regions calcium components and "yellow" for regions of the fat components). Thereby, it is easy to compare the components of the vital tissue on the MPR image with those on the cross-sectional image and/or expanded image, allowing the vital tissue, which has become a calcified component or lipid component, to be easily viewed.

In FIG. 17, an MPR image "M" when the tubular portion 1 is cut into sections along the central axis at the position of the cross-section "A" is shown. Further, in FIG. 17, the central axis of the tubular portion 1 represented on the MPR image is indicated as "L0," the line along the central axis L0 as "L1," and the line perpendicular to the line L1 as "L2."

[The Fifth Embodiment]

In the fourth embodiment described above, the expanded image and the MPR image were indicated as images of the vital tissue to be displayed along with the cross-sectional image. In contrast to this, in this fifth embodiment, it is indicated that a view image is displayed in conjunction with the expanded image and the MPR image. In addition, the view image may be displayed instead of the expanded image and/or MPR image.

Figure 18:
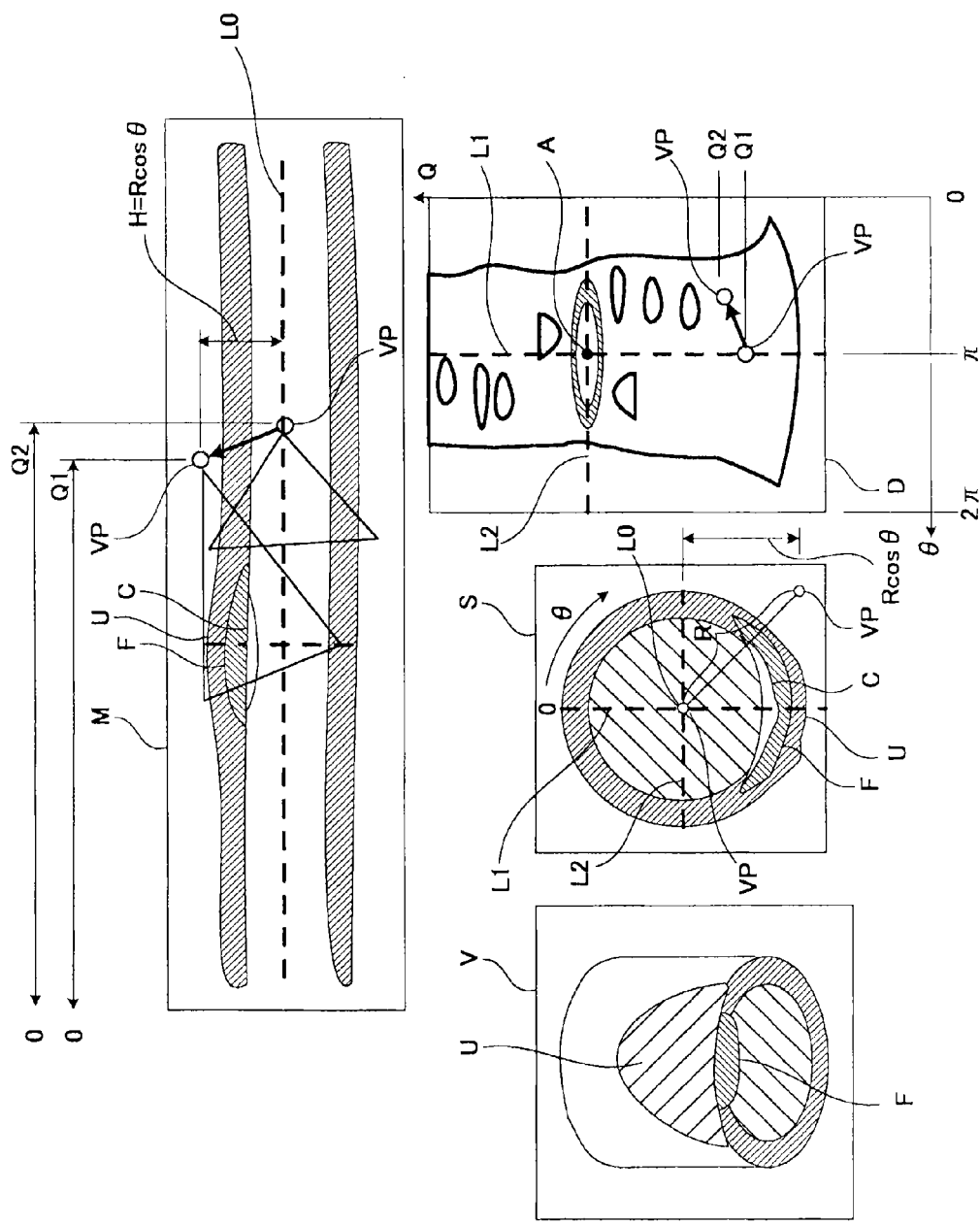
FIG. 18 is a diagram showing an example of the display modes when a cross-sectional image is displayed along with an expanded image, an MPR image, and a view image in the medical image diagnosis apparatus according to the fifth embodiment.

Next, a medical image diagnosis apparatus according to the fifth embodiment is described with reference to FIG. 18. FIG. 18 is a diagram showing an example of the display modes when a cross-sectional image is displayed along with an expanded image, an MPR image, and a view image in the medical image diagnosis apparatus according to the fifth embodiment. In addition, the configuration of the fifth embodiment different from the embodiments described above is mainly described, with the descriptions of the configuration similar to the embodiments described above omitted.

In this embodiment, the image generator 16 comprises a view image generator 174. The view image generator 174 creates view images showing the outside of the tubular portion 1 when the tubular portion 1 is viewed from the point of view based on the three-dimensional medical image data. Moreover, view images showing the inside of the tubular portion 1 may be created with the point of view placed in the tubular portion 1.

Regarding the creation of view images, a known technique (e.g. Japanese Unexamined Patent Application Publication No. 2006-346177 publication) is used. In the publication, a means of setting a plurality of points of view in a predetermined mode (fly-through mode) based on MPR image data, and a means of performing rendering processing on the volume data of wall information based on the information of the set points of view to generate fly-through image data. Using this technique to generate a fly-through image, a view image can be created. In addition, the point of view and range of sight can be designated by a user, and the controller 13, in response to the operation of the operating unit (input section) 18 by the user, stores the point of view and range of sight in the memory unit 14.

Here, the point of view is described with reference to FIG. 18. In FIG. 18, the cross-sectional image is indicated as "S," the expanded image as "D," the MPR image as "M," the view image as "V," the central axis of the tubular portion 1 as "L0," and the point of view as "VP." Moreover, in the cross-sectional image S, the top position is defined as an origin "0," the angle from the origin 0 in the clockwise direction as "θ," and the distance from the central axis L0 to the point of view VP as "R." Further, in the expanded image D. a distance (P) from the origin 0 along the central axis L0 is taken in the longitudinal axis, a rotational angle "θ" from the origin 0 in the clockwise direction is taken in the horizontal axis, and movement of the point of view VP is indicated by the arrow (movement from "Q1" to "Q2" for the position on the line L1). Further, in the MPR image M, the movement of the point of view VP is indicated by the arrow (movement from "Q1" to "Q2" for the position on the central axis L0).

The position of the point of view VP on the cross-sectional image S is represented by the rotational angle θ around the central axis L0 and the distance R from the central axis L0. In contrast to this, the position of the point of view VP on the expanded image D is represented by the position Q on the central axis L0 (the distance from the origin 0), and the rotational angle θ from the origin 0. Further, the position of the point of view VP on the MPR image M is represented by the position Q on the central axis L0 and the height H (the distance from the line L2). In addition, it is expressed by H=R*cosθ.

Thus, respective positions of the point of view VP on the expanded image D and the point of view VP on the MPR image M can both be represented by P, θ, and R. Namely. when the expression for the position of the point of view VP on the expanded image D is defined as f (P, θ, R), the position of the point of view VP on the expanded image D can be obtained by substituting values P, θ, and R in that expression. This means that P, θ, and R can be derived from the position of the point of view VP on the expanded image D using f (P, θ, R).

Moreover, when the expression for the position of the point of view VP on the MPR image M is defined as g (P, θ, R), the position of the point of view VP on the MPR image M can be obtained by substituting values P, θ, and R in the expression. This means that P, θ, and R can be derived from the position of the point of view VP on the MPR image M using g (P, θ, R).

That is, the position of the point of view VP on the MPR image M can be obtained from the position of the point of view VP on the expanded image D. Moreover, the position of the point of view VP on the expanded image D can be obtained from the position of the point of view VP on the MPR image M.

The display controller 21, in response to the operation by the operating unit (input section) 18, causes the point of view to be displayed on the MPR image in a movable manner.

Further, the display controller 21 causes the point of view to be displayed on the expanded image, in addition to causing the point of view on the expanded image to be displayed in conjunction with the point of view on the MPR image.

Thus, in response to the operation by the operating unit (input section) 18, as the display controller 21 moves the point of view of any one of the expanded images and the MPR image, in response to the moved position of that point of view, the means can move and display the point of view of the other image.

Further, the display controller 21 causes a form including a concave portion and/or a convex portion of the outer wall 3 of the tubular portion 1 to be displayed in a view image (indicated as "V" in FIG. 18). In this case, the display controller 21 causes the concave portion and the convex portion to be displayed in a distinguishable manner. The concave portion and the convex portion (indicated as "U" in FIG. 18) may be distinguished using colors different from each other, and may be distinguished by shades or hatching different from each other. In addition, the concave portion in the inner wall 2 of the tubular portion 1 refers to a concave site from the estimated normal inner wall 2a, while the convex portion refers to a site that is raised from the normal inner wall 2a, with both the concave portion and the convex portion being determined from the three-dimensional data of medical images. Further, the concave portion in the outer wall 3 of the tubular portion 1 refers to a concave site from the estimated normal outer wall 3a, while the convex portion refers to a site that is raised from the normal outer wall 3a, with both the concave portion and the convex portion being determined from the three-dimensional data of medical images.

[The Sixth Embodiment]

In the fifth embodiment described above, the expanded image, the MPR image, and the view image were indicated as images of the vital tissue to be displayed along with the cross-sectional image. In contrast to this, in the sixth embodiment, it is indicated that an MPR and an expanded image of the outer wall are displayed. In addition, the expanded image of the outer wall may be displayed instead of the MPR image, and may be displayed in conjunction with the expanded image and/or view image.

Figure 19:
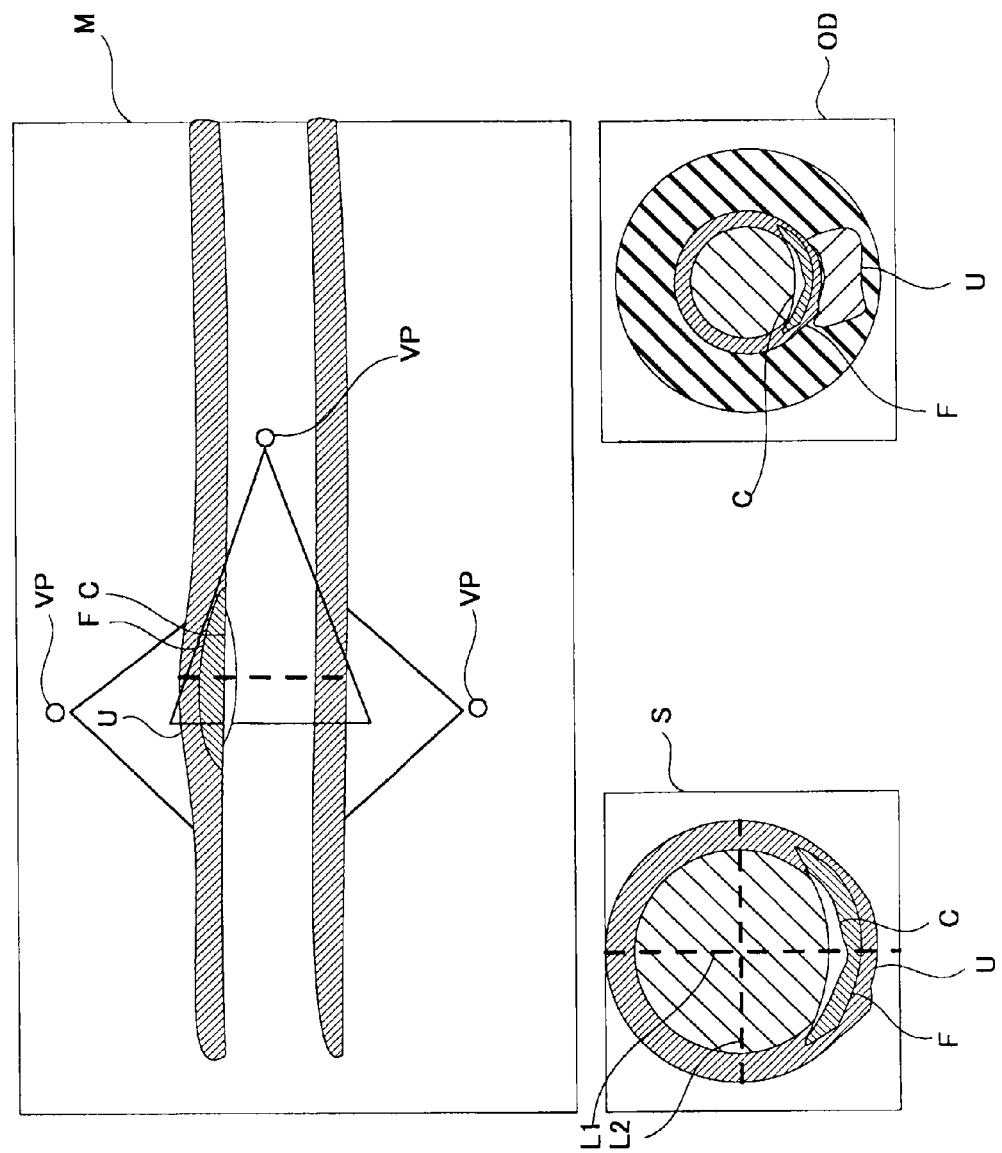
FIG. 19 is a diagram showing an example of the display modes when a cross-sectional image is displayed along with an MPR image and an expanded image of the outer wall in the medical image diagnosis apparatus according to the sixth embodiment.

Next, a medical image diagnosis apparatus according to the sixth embodiment is described with reference to FIG. 19. FIG. 19 is a diagram showing an example of the display modes when a cross-sectional image is displayed along with an MPR image and an expanded image of the outer wall in the medical image diagnosis apparatus according to the sixth embodiment. In addition, the configuration of the sixth embodiment different from the embodiments described above is mainly described, with the descriptions of the configuration similar to the embodiments described above omitted.

In this embodiment, the image generator 16 comprises an outer wall-expanded mage generator 175. The outer wall-expanded image generator 175 generates an expanded image of the outer wall representing that the outer wall 3 of the tubular portion 1 appears to be opened outside the cross-sectional image (extended in the radial direction from the central axis L0). In addition, the length to be extended is the length of a portion of the outer wall 3 falling within the range of sight.

The display controller 21 causes the cross-sectional image to be displayed along with the MPR image and the expanded image of the outer wall. In the expanded image of the outer wall, the display controller 21 causes a form including a concave portion and/or a convex portion of the outer wall 3 of the tubular portion 1 to be displayed. In this case, the display controller 21 causes the concave portion and the convex portion (indicated as "U" in FIG. 18) to be displayed in a distinguishable manner. The concave portion and the convex portion may be distinguished with colors different from each other, and may be distinguished with shades or hatching different from each other. In addition, also in the expanded image of the outer wall, similar to the view image, the concave portion in the inner wall 2 of the tubular portion 1 refers to a concave site from the estimated normal inner wall 2a, and the convex portion refers to a site that is raised from the normal inner wall 2a, with both the concave portion and the convex portion being determined from the three-dimensional data of medical images. Further, the concave portion in the outer wall 3 of the tubular portion 1 refers to a concave site from the estimated normal outer wall 3a, while the convex portion refers to a site that is raised from the normal outer wall 3a, with both the concave portion and the convex portion being determined from the three-dimensional data of medical images.

In FIG. 19, the expanded image of the outer wall "OD" is indicated. By causing the expanded image of the outer wall to be displayed, the lesion having developed in the outer wall 3 (which corresponds to the site indicated as "U" in FIG. 19) can be found while viewing the vital tissue on the inner wall 2.

[The Seventh Embodiment]

In the sixth embodiment described above, it was indicated that the cross-sectional image is displayed along with the MPR image and the expanded image of the outer wall. In contrast to this, in the seventh embodiment, it is indicated that an MPR and an expanded image of the outer wall are displayed along with an expanded image.

Figure 20:
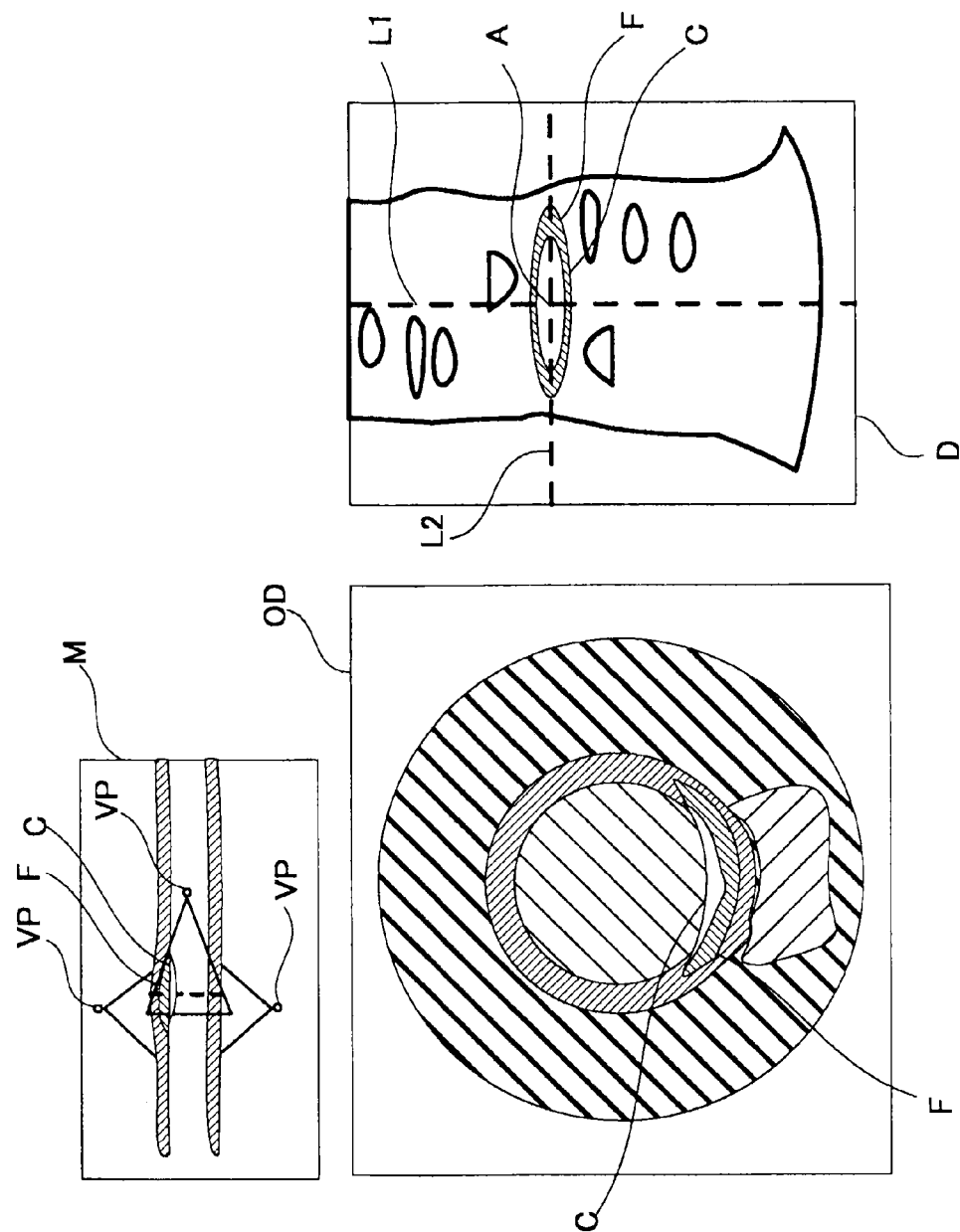
FIG. 20 is a diagram showing an example of the display modes when an expanded image is displayed along with an MPR image and an expanded image of the outer wall in the medical image diagnosis apparatus according to the seventh embodiment.

Next, a medical image diagnosis apparatus according to the seventh embodiment is described with reference with FIG. 20. FIG. 20 is a diagram showing an example of the display modes when an expanded image is displayed along with an MPR image and an expanded image of the outer wall in the medical image diagnosis apparatus according to the seventh embodiment. In addition, the configuration of the seventh embodiment different from the embodiments described above is mainly described, with the descriptions of the configuration similar to the embodiments described above omitted.

As shown in FIG. 20, the display controller 21 causes an expanded image to be displayed along with an MPR image and an expanded image of the outer wall. By causing the expanded image and the expanded image of the outer wall to be displayed, respective vital tissues of the inner wall 2 and the outer wall 3 of the tubular portion 1 can be checked simultaneously. Thereby, based on the lesion developing in either the inner wall 2 or the outer wall 3, seeing whether any lesion has developed in the wall opposite to one wall where the lesion has developed can be easily checked by viewing the other vital tissue simultaneously.

Although several embodiments of the present invention have been described, these embodiments are presented as examples and are not intended to limit the range of the invention. These novel embodiments can be implemented in other various forms, and various omissions, replacements, and changes can be made without departing from the scope of the invention. These embodiments and variations thereof are included in the range and scope of the invention, as well as included in the invention described in Claims and the range of the equivalents thereof.

EXPLANATION OF SYMBOLS

1 Tubular portion
2 Inner wall
3 Outer wall
4 Core line
4a Centroid
N First raised portion
P Second raised portion
B Third raised portion
11 Imaging unit
12 Communication unit
13 Controller
14 Memory unit
15 Data converting unit
16 Image generator
17 Image synthesizer
18 Operating unit
21 Display controller
22 Display unit
161 Expanded image generator
162 Inner wall extractor
163 Outer wall extractor
164 Normal inner wall estimator
165 Normal outer wall estimator
166 First raised portion calculator
167 Second raised portion calculator
168 Color mapping unit
171 Cross-sectional image generator
172 Color-coder
173 MPR-image generator
174 View-image generator
175 Outer wall-expanded image generator

The invention claimed is:

1. A medical image diagnosis apparatus comprising:
an imaging unit configured to acquire three-dimensional medical image data of vital tissues having an inner wall and an outer wall by imaging the vital tissue;
an inner wall extractor configured to extract the inner wall of the vital tissue based on the medical image data;
an outer wall extractor configured to extract the outer wall of the vital tissue based on the medical image data;
a first raised portion calculator configured to obtain information including the presence of a first raised portion in which the inner wall of the vital tissue is raised inward, based on the extracted inner wall of the vital tissue;
a second raised portion calculator configured to obtain information including the presence of a second raised portion in which the outer wall of the vital tissue is raised outward, based on the extracted outer wall of the vital tissue; and
a display controller configured to superimpose the information of the first raised portion obtained by the first raised portion calculator and the information of the second raised portion obtained by the second raised portion calculator on an image of the vital tissue, and cause the image to be displayed on a display unit.

2. The medical image diagnosis apparatus according to claim 1, wherein the display controller is configured to cause each piece of information of the first raised portion and the second raised portion to be displayed in a distinguishable manner.

3. The medical image diagnosis apparatus according to claim 1, further comprising:
a normal inner wall estimator configured to estimate a normal inner wall in the shape of the inner wall before being raised, based on the extracted inner wall of the vital tissue; and
a normal outer wall estimator configured to estimate a normal outer wall in the shape of the outer wall before being raised, based on the extracted outer wall of the vital tissue;
wherein:
the first raised portion calculator is configured to obtain a first thickness, which is the height that the first raised portion is raised from the normal inner wall;
the second raised portion calculator is configured to obtain a second thickness, which is the height that the second raised portion is raised from the normal outer wall; and
the display controller is configured to cause the obtained first thickness to be displayed as information of the first raised portion, and cause the obtained second thickness to be displayed as information of the second raised portion.

4. The medical image diagnosis apparatus according to claim 3, further comprising:
a color mapping unit configured to create a first color for the first thickness, and a second color corresponding to the second thickness, which is different from the first color;
wherein the display controller is configured to cause each piece of information of the first raised portion and the second raised portion to be displayed according to the first color and the second color.

5. The medical image diagnosis apparatus according to claim 4, wherein the color mapping unit is configured to create the first color by dividing the first thickness in the thickness direction by stages and color-coding of each stage, and create the second color by dividing the second thickness in the thickness direction by stages and color-coding of each stage.

6. The medical image diagnosis apparatus according to claim 1, wherein:
the inner wall extractor is configured to extract the inner wall of the vital tissue including a tubular portion;
the outer wall extractor is configured to extract the outer wall of the vital tissue including the tubular portion; and the display controller is configured to cause the information of the second raised portion superimposed on an image of the inner wall of the tubular portion to be displayed.

7. The medical image diagnosis apparatus according to claim 1, further comprising:
   a cross-sectional image generator configured to create a cross-sectional image when the vital tissue is cut into sections at a designated position based on the medical image data; and
   a color-coder configured to classify components of the vital tissue in the created cross-sectional image, to color-code the components by the classification;
   wherein the display controller is configured to cause the cross-sectional image color-coded by the color-coder to be displayed.

8. The medical image diagnosis apparatus according to claim 7, further comprising:
   an expanded image generator configured to generate an expanded image in which the inner wall of a tubular portion is expanded in a planar manner;
   wherein:
   the display controller is configured to cause the generated expanded image to be displayed, and cause the position on the expanded image to be displayed such that the position can be designated by operating an input section;
   the cross-sectional image generator is configured to, in response to the designation, create the cross-sectional image when the vital tissue is cut into sections at the designated position; and
   the display controller is configured to cause the created expanded image to be displayed along with the cross-sectional image.

9. The medical image diagnosis apparatus according to claim 8, wherein:
   the color-coder is configured to classify components of the vital tissue in the expanded image, to color-code the components by the classification; and
   the display controller is configured to cause the color-coded expanded image to be displayed.

10. The medical image diagnosis apparatus according to claim 8, further comprising:
    an MPR-image generator configured to create an MPR image representing a plurality of cross-sections of the vital tissue based on the medical image data;
    wherein the display controller is configured to cause the MPR image to be displayed along with the cross-sectional image and the expanded image.

11. The medical image diagnosis apparatus according to claim 10, wherein:
    the color-coder is configured to classify components of the vital tissue in the MPR image, to color-code the components by the classification; and
    the display controller is configured to cause the color-coded MPR image to be displayed.

12. The medical image diagnosis apparatus according to claim 11, wherein the display controller is further configured to cause a point of view designated based on the medical image data to be displayed on the MPR image.

13. The medical image diagnosis apparatus according to claim 12, wherein the display controller is configured to, in response to operating the input section, cause the point of view to be displayed in a movable manner.

14. The medical image diagnosis apparatus according to claim 13, wherein the display controller is further configured to cause the point of view to be displayed on the expanded image, and cause the point of view on the expanded image to be displayed in conjunction with the point of view on the MPR image.

15. The medical image diagnosis apparatus according to claim 10, further comprising:
    an outer wall-expanded image generator configured to generate an expanded image of the outer wall that represents the outer wall of the tubular portion appearing to be opened outside the cross-sectional image; and
    the display controller configured to cause the generated expanded image of the outer wall to be displayed along with the cross-sectional image and the MPR image.

16. The medical image diagnosis apparatus according to claim 15, wherein the display controller is further configured to cause a shape including a concave portion and/or a convex portion of the outer wall of the tubular portion in the expanded image of the outer wall to be displayed, and cause the concave portion and the convex portion to be displayed in a distinguishable manner.

17. The medical image diagnosis apparatus according to claim 10, further comprising:
    a view-image generator configured to create a view image that shows the outside of the tubular portion when seeing the tubular portion from a designated point of view based on the medical image data;
    wherein the display controller is configured to cause the created view image to be displayed along with the cross-sectional image, the expanded image, and the MPR image.

18. The medical image diagnosis apparatus according to claim 17, wherein the display controller is further configured to cause a shape including a concave portion and/or a convex portion of the outer wall of the tubular portion to be displayed in the view image, and cause the concave portion and the convex portion to be displayed in a distinguishable manner.

19. A medical image display apparatus, comprising:
    an inner wall extractor configured to extract an inner wall of a vital tissue, based on three-dimensional medical image data of the vital tissue including the inner wall and an outer wall acquired externally;
    an outer wall extractor configured to extract the outer wall of the vital tissue based on the medical image data;
    a first raised portion calculator configured to obtain information of a first raised portion in which the inner wall of the vital tissue is raised inward, based on the inner wall of the vital tissue;
    a second raised portion calculator configured to obtain information of a second raised portion in which the outer wall of the vital tissue is raised outward, based on the outer wall of the vital tissue; and
    a display controller configured to superimpose the information of the first raised portion obtained by the first raised portion calculator and the information of the second raised portion obtained by the second raised portion calculator on an image of the vital tissue, and cause the image to be displayed on a display unit.

20. The medical image diagnosis apparatus according to claim 7, wherein:
    the color-coder is configured to classify calcium or fat as components of the vital tissue based on brightness values.

* * * * *